US011712056B2

(12) United States Patent
Peltier et al.

(10) Patent No.: US 11,712,056 B2
(45) Date of Patent: Aug. 1, 2023

(54) EXTRACT OBTAINED FROM SEVERAL PLANTS FOR USE IN THE PREVENTION AND/OR TREATMENT OF CHRONIC INFLAMMATORY BOWEL DISEASES

(71) Applicants: VALBIOTIS, Perigny (FR); UNIVERSITE CLERMONT AUVERGNE, Clermont Ferrand (FR)

(72) Inventors: Sébastien Peltier, Fouras (FR); Pascal Sirvent, Ceyrat (FR); Yolanda Otero, Antoingt (FR)

(73) Assignees: VALBIOTIS, Perigny (FR); UNIVERSITE CLERMONT AUVERGNE, Clermont Ferrand (FR)

( * ) Notice: Subject to any disclaimer, the term of this patent is extended or adjusted under 35 U.S.C. 154(b) by 177 days.

(21) Appl. No.: 16/962,277

(22) PCT Filed: Jan. 18, 2019

(86) PCT No.: PCT/EP2019/051227
§ 371 (c)(1),
(2) Date: Jul. 15, 2020

(87) PCT Pub. No.: WO2019/141802
PCT Pub. Date: Jul. 25, 2019

(65) Prior Publication Data
US 2020/0359670 A1 Nov. 19, 2020

(51) Int. Cl.
| | | |
|---|---|---|
| *A23L 33/11* | (2016.01) | |
| *A61K 31/05* | (2006.01) | |
| *A61K 31/216* | (2006.01) | |
| *A61K 31/4525* | (2006.01) | |
| *A61K 31/519* | (2006.01) | |
| *A61K 31/7048* | (2006.01) | |
| *A61K 36/287* | (2006.01) | |
| *A61K 36/45* | (2006.01) | |
| *A61K 36/63* | (2006.01) | |
| *A61K 36/67* | (2006.01) | |

(52) U.S. Cl.
CPC .............. *A23L 33/11* (2016.08); *A61K 31/05* (2013.01); *A61K 31/216* (2013.01); *A61K 31/4525* (2013.01); *A61K 31/519* (2013.01); *A61K 31/7048* (2013.01); *A61K 36/287* (2013.01); *A61K 36/45* (2013.01); *A61K 36/63* (2013.01); *A61K 36/67* (2013.01)

(58) Field of Classification Search
CPC ....... A23L 33/11; A61K 31/05; A61K 31/216; A61K 31/4525; A61K 31/519; A61K 31/7048; A61K 36/287; A61K 36/45; A61K 36/63; A61K 36/67
See application file for complete search history.

(56) References Cited

U.S. PATENT DOCUMENTS

| | | | |
|---|---|---|---|
| 2002/0012708 A1 | 1/2002 | Ruepp | |
| 2004/0219232 A1* | 11/2004 | Lipton | A61K 38/34 424/725 |
| 2009/0285911 A1* | 11/2009 | Bombardelli | A61P 9/10 514/468 |
| 2013/0303468 A1* | 11/2013 | Fujii | A61P 25/20 514/23 |
| 2016/0256507 A1* | 9/2016 | Lo Franco | A23L 2/087 |

FOREIGN PATENT DOCUMENTS

| | | | |
|---|---|---|---|
| CN | 103690537 A | * 4/2014 | |
| EP | 2135616 A1 | * 12/2009 | A21D 2/36 |
| WO | WO2016062958 A1 | 4/2016 | |
| WO | WO2016156527 A1 | 10/2016 | |

OTHER PUBLICATIONS

Ana Cristina Alves de Almeida, et al. "Recent Trends in Pharmacological Activity of Alkaloids in Animal Colitis: Potential Use for Inflammatory Bowel Disease," Evidence-Based Complementary and Alternative Medicine vol. 2017, 1-24. (Year: 2017).*
Machine_Translation_EP2135616 (Year: 2022).*
CDC/ Disease of the Week—Inflammatory Bowel Disease (downloaded Jul. 12, 2022 from https://web.archive.org/web/20170519081232/https://www.cdc.gov/dotw/ibd/index.html). Available on the internet May 19, 2017. (Year: 2017).*
L. Panizzi and M.L. Scarpati. "Constitution of Cynarine, the Active Principle of the Artichoke," Nature, 1954, 1062. (Year: 1954).*
Machine translation of EP2135616 (A1), provided by EPO (Year: 2022).*
Machine translation of CN103690537(A), provided by EPO (Year: 2022).*
A. Romani, et al. "Characterization of Violetta di Toscana, a typical Italian variety of artichoke (*Cynara scolymus* L.)," Food Chemistry 95 (2006) 221-225. (Year: 2006).*
Biedermann et al, "Bilberry ingestion improves disease activity in mild to moderate ulcerative colitis—An open pilot study", Journal of Crohn's and Colitis, Elsevier BV, Aug. 9, 2012, pp. 271-279, vol. 7, No. 4.
Tharmalingam et al, "Inhibitory effect of piperine on Helicobacter pylori growth and adhesion to gastric adenocarcinoma cells", Infectious Agents and Cancer, Biomed Central Ltd, Dec. 16, 2014, pp. 1-10, vol. 9, No. 43.
Tao et al, "Polysaccharides from Chrysanthemum morifolium Ramat ameliorate colitis rats by modulating the intestinal microbiota community", Oncotarget, Oct. 6, 2017, pp. 80790-80803, vol. 8, No. 46.

* cited by examiner

*Primary Examiner* — Michael P Cohen
(74) *Attorney, Agent, or Firm* — Greer, Burns & Crain, Ltd.

(57) ABSTRACT

The invention relates to a composition comprising at least one specific mixture of molecules for use as a drug or nutritional product in the prevention and/or treatment of chronic inflammatory bowel diseases in humans or animals.

15 Claims, No Drawings

EXTRACT OBTAINED FROM SEVERAL PLANTS FOR USE IN THE PREVENTION AND/OR TREATMENT OF CHRONIC INFLAMMATORY BOWEL DISEASES

CROSS-REFERENCE TO RELATED APPLICATIONS

This application is the U.S. National phase application corresponding to PCT/EP2019/051227 which was assigned an international filing date of Jan. 18, 2019 and associated with publication WO 2019/141802 A1 and which claims priority to French patent application FR 1870047 filed on Jan. 19, 2018, the disclosures of which are expressly incorporated herein by reference.

TECHNICAL FIELD

The present invention relates to an extract obtained from several plants for use as a drug or nutritional product in the prevention and/or treatment of chronic inflammatory bowel diseases (IBD).

BACKGROUND

IBD, like Crohn's disease or ulcerative colitis, are conditions characterized by an inflammation of the lining of a part of the digestive tract related to an overactive digestive immune system. Symptoms are usually characterized by chronic abdominal pain, diarrhea and weight loss. These diseases progress through inflammatory attacks of extremely variable duration and frequency depending on the patient. These attacks alternate with phases of remission.

Most of the time, clinical management enables lasting control of the disease and a satisfactory quality of life other than during attacks, but there is no curative treatment. In addition, it is known that current treatments have side effects on bone density, weight gain and even exacerbate the intestinal disease (Asl Baakhtari 5, McCombie A, Ten Bokkel Huinink S, Irving P, Siegel C A, Mulder R, et al. *Observational Study of Perspectives of Inflammatory Bowel Disease Patients Concerning the Use of Corticosteroids. Dig Dis.* 2018; 36(1):33-9. Epub 2017/09/04. doi: 10.1159/000478772. PubMed PMID: 28866661; Waljee A K, Wiitala W L, Govani 5, Stidham R, Saini 5, Hou J, et al. *Corticosteroid Use and Complications in a US Inflammatory Bowel Disease Cohort. PLoS One.* 2016; 11(6):e0158017. Epub 2016/06/24. doi: 10.1371/journal.pone.0158017. PubMed PMID: 27336296; PubMed Central PMCID: PMCPMC4918923).

IBD patients are often thin and even malnourished due to malabsorption associated with inflammation, but recent studies report increasing numbers of overweight patients with IBD and associate obesity with a more severe course of the illness (Hass D J, Brensinger C M, Lewis J D, Lichtenstein G R. *The impact of increased body mass index on the clinical course of Crohn's disease. Clin Gastroenterol Hepatol.* 2006; 4(4):482-8. Epub 2006/04/18. doi: 10.1016/j.cgh.2005.12.015. PubMed PMID: 16616354; Blain A, Caftan 5, Beaugerie L, Carbonnel F, Gendre J P, Cosnes J. *Crohn's disease clinical course and severity in obese patients. Clin Nutr.* 2002; 21(1):51-7. Epub 2002/03/09. doi: 10.1054/clnu.2001.0503. PubMed PMID: 11884013). Several studies conducted on mouse models have also shown that a high-fat diet promotes intestinal inflammation at the cellular level (Ding S, Chi M M, Scull B P, Rigby R, Schwerbrock N M, Magness S, et al. *High-fat diet: bacteria interactions promote intestinal inflammation which precedes and correlates with obesity and insulin resistance in mouse. PLoS One.* 2010; 5(8):e12191. Epub 2010/09/03. doi: 10.1371/journal.pone.0012191. PubMed PMID: 20808947; PubMed Central PMCID: PMCPMC2922379) and disrupts the intestinal barrier function (Lam Y Y, Ha C W, Campbell C R, Mitchell A J, Dinudom A, Oscarsson J, et al. *Increased gut permeability and microbiota change associate with mesenteric fat inflammation and metabolic dysfunction in diet-induced obese mice. PLoS One.* 2012; 7(3):e34233. Epub 2012/03/30. doi: 10.1371/journal.pone.0034233. PubMed PMID: 22457829; PubMed Central PMCID: PMCPMC3311621).

The development of IBD is actually linked to several factors (genetic and environmental), in particular changes in the composition of the microbiota and the immune response (Parekh P J, Balart L A, Johnson D A. *The Influence of the Gut Microbiome on Obesity, Metabolic Syndrome and Gastrointestinal Disease. Clin Trans' Gastroenterol.* 2015; 6:e91. Epub 2015/06/19. doi: 10.1038/ctg.2015.16. PubMed PMID: 26087059; PubMed Central PMCID: PMCPMC4816244; Jostins L, Ripke 5, Weersma R K, Duerr R H, McGovern D P, Hui K Y, et al. *Host-microbe interactions have shaped the genetic architecture of inflammatory bowel disease. Nature.* 2012; 491(7422):119-24. Epub 2012/11/07. doi: 10.1038/nature11582. PubMed PMID: 23128233; PubMed Central PMCID: PMCPMC3491803). It is known in particular that patients with IBD have an intestinal dysbiosis characterized by a decrease in Bacteroidetes and an increase in Firmicutes (Rigottier-Gois L. *Dysbiosis in inflammatory bowel diseases: the oxygen hypothesis. ISME J.* 2013; 7(7):1256-61. Epub 2013/05/17. doi: 10.1038/ismej.2013.80. PubMed PMID: 23677008; PubMed Central PMCID: PMCPMC3695303; Martinez-Medina M, Denizot J, Dreux N, Robin F, Billard E, Bonnet R, et al. *Western diet induces dysbiosis with increased E coli in CEABAC10 mice, alters host barrier function favouring AIEC colonisation. Gut.* 2014; 63(1):116-24. Epub 2013/04/20. doi: 10.1136/gutjnl-2012-304119. PubMed PMID: 23598352). This dysbiosis affects the homeostasis of the host due to colonization by bacteria secreting pro-inflammatory cytokines such as TNF-α (Agus A, Denizot J, Thevenot J, Martinez-Medina M, Mossier S, Sauvanet P, et al. *Western diet induces a shift in microbiota composition enhancing susceptibility to Adherent-Invasive E. coli infection and intestinal inflammation. Sci Rep.* 2016; 6:19032. Epub 2016/01/09. doi: 10.1038/srep19032. PubMed PMID: 26742586; PubMed Central PMCID: PMCPMC4705701). Moreover, recently studies have shown a reduction in the abundance of *Akkermansia municiphila* in several human diseases, including IBD (Berry D, Reinisch W. *Intestinal microbiota: a source of novel biomarkers in inflammatory bowel diseases? Best Pract Res Clin Gastroenterol.* 2013; 27(1):47-58. Epub 2013/06/19. doi: 10.1016/j.bpg.2013.03.005. PubMed PMID: 23768552.). Furthermore, in a mouse model fed a high-fat diet with spontaneous colitis, the decrease in the abundance of *Akkermansia Municiphila* was correlated with an alteration of the integrity of the mucous barrier and an increase in the severity of colitis (Gulhane M, Murray L, Lourie R, Tong H, Sheng Y H, Wang R, et al. *High Fat Diets Induce Colonic Epithelial Cell Stress and Inflammation that is Reversed by IL-22. Sci Rep.* 2016; 6:28990. Epub 2016/06/29. doi: 10.1038/srep28990. PubMed PMID: 27350069; PubMed Central PMCID: PMCPMC4924095). On the other hand, a mouse model with IBD treated with extracellular vesicles from *Akkermansia municiphila* showed an improvement on the inflammatory infiltration of the wall of the colon as well as the protection against the development of colitis (Kang C S, Ban M, Choi E J, Moon H G, Jeon J S, Kim D K, et al. *Extracellular vesicles derived from gut microbiota, especially Akkermansia muciniphila, protect the progression of dextran sulfate sodium-induced colitis*. PLoS One. 2013; 8(10):e76520. Epub 2013/11/10. doi: 10.1371/ journal.pone.0076520. PubMed PMID: 24204633; PubMed Central PMCID: PMCPMC3811976.). Other bacteria, such as *Roseburia* spp, for example, have also been involved in the pathophysiology of IBD. A significant reduction in the proportion of *Roseburia* spp in IBD was notably highlighted, which could contribute to the dysfunctions of the immune system and the pro-inflammatory state found in these pathologies (Tamanai-Shacoori Z, Smida I, Bousarghin L, Loreal O, Meuric V, Fong S, Bonnaure-Mallet M, Jolivet-Gougeon A *Roseburia* spp.: *a marker of health?*. Future Microbiol. 2017; 12:157-170. doi: 10.2217/fmb-2016-0130. PubMed PMID: 28139139).

SUMMARY

The object of the invention is to provide a product capable of modulating the proportion of bacteria involved in the pathophysiology of IBD, such as *Akkermansia municiphila* or *Roseburia* spp, and/or to improve the Bacteroidetes/ Firmicutes ratio in the intestinal microbiota so as to be effective in the prevention and/or treatment of IBD.

To address this, the invention relates to the use of a composition comprising a mixture of molecules consisting of at least one extract obtained from several plant-derived raw materials. In particular, the subject matter of the invention is a composition comprising at least one mixture of molecules consisting of at least:
- a single extract obtained from a mixture of at least two plants chosen from *Chrysanthellum indicum, Cynara scolymus, Vaccinium myrtillus* and *Piper;*
- and, if the mixture of plants from which the single extract is obtained does not include *Chrysanthellum indicum*, an extract of *Chrysanthellum indicum* or an extract obtained from at least two plants comprising *Chrysanthellum indicum;*
- and, if the mixture of plants from which the single extract is obtained does not include *Cynara scolymus*, an extract of *Cynara scolymus* or an extract obtained from at least two plants comprising *Cynara scolymus;*
- and, if the mixture of plants from which the single extract is obtained does not include *Vaccinium myrtillus*, an extract of *Vaccinium myrtillus* or an extract obtained from at least two plants comprising *Vaccinium myrtillus;*
- and, if the mixture of plants from which the single extract is obtained does not include *Piper*, piperine or an extract of *Piper* or an extract obtained from at least two plants comprising *Piper;* for use as a drug or nutritional product in the prevention and/or treatment of chronic inflammatory bowel disease in humans or animals.

It may, for example, relate to a composition comprising at least one mixture of molecules consisting of at least:
- a single extract obtained from at least *Chrysanthellum indicum, Cynara scolymus* and *Vaccinium myrtillus* and *Piper*; and/or
- a single extract obtained from at least *Chrysanthellum indicum, Cynara scolymus* and *Vaccinium myrtillus* and piperine;

for use as a drug or nutritional product in the prevention and/or treatment of inflammatory bowel diseases in humans or animals, in particular Crohn's disease and/or ulcerative colitis.

Such a composition is known for its effects on carbohydrate and/or lipid metabolism, but surprisingly, according to the invention, it is capable of modifying the profile of the intestinal microbiota by reducing the Bacteroidetes/Firmicutes ratio and increasing the abundance of *Akkermansia municiphila, Roseburia* spp, and constitutes an effective drug for the prevention and/or treatment of IBD.

The invention is hereby described in detail.

DETAILED DESCRIPTION

Definitions

"Single extract" or "unit extract" or "extract obtained from several plants "X" or plant-derived raw materials "X"" or "single extract obtained from several plants "X" or plant-derived raw materials "X"" within the meaning of the invention means a set of molecules obtained from a mixture of at least two plants "X" by any suitable process. In particular, the following may be cited: aqueous extracts (obtained using an aqueous solvent), alcoholic extracts (obtained using an alcoholic solvent) or extracts using an organic solvent, or using a natural fatty substance or a mixture of natural fatty substances, in particular a plant-derived oil or a mixture of plant-derived oils.

"Extract of a plant "X"" within the meaning of the invention means a set of molecules obtained from a single plant "X" by any suitable method. In particular, the following may be cited: aqueous extracts (obtained using an aqueous solvent), alcoholic extracts (obtained using an alcoholic solvent) or extracts using an organic solvent, or using a natural fatty substance or a mixture of natural fatty substances, in particular a plant-derived oil or a mixture of plant-derived oils.

"Plant" or "plant-derived raw material" within the meaning of the invention means the whole plant or part of a plant, including cell cultures, which has not yet undergone specific treatment and is intended to be used in the manufacturing of a plant preparation.

"Mixture of plants of the single extract" within the meaning of the invention means the mixture of plants from which the single extract is obtained.

"Aqueous solvent" within the meaning of the invention means any solvent consisting entirely or partly of water. Thus, the following may be cited: water itself, hydroalcoholic solvents in any proportion or even solvents consisting of water and of a compound such as glycerin or propylene glycol in any proportion. Among the alcoholic solvents, ethanol in particular may be cited.

The invention therefore relates to a composition comprising at least one mixture of molecules consisting of at least:
- an extract, called a "single extract", obtained from a mixture of at least two plants chosen from *Chrysanthellum indicum, Cynara scolymus, Vaccinium myrtillus* and *Piper*, preferably a single extract obtained from a mixture of at least three or four plants chosen from *Chrysanthellum indicum, Cynara scolymus, Vaccinium myrtillus* and *Piper;*
- and, if the mixture of plants of the single extract does not include *Chrysanthellum indicum*, an extract of *Chrysanthellum indicum* or an extract obtained from at least two plants comprising *Chrysanthellum indicum;* and, if the mixture of plants of the single extract does not include *Cynara scolymus*, an extract of *Cynara scolymus* or an extract obtained from at least two plants comprising *Cynara scolymus*;

and, if the mixture of plants of the single extract does not include *Vaccinium myrtillus*, an extract of *Vaccinium myrtillus* or an extract obtained from at least two plants comprising *Vaccinium myrtillus*;

and, if the mixture of plants of the single extract does not include *Piper*, piperine or an extract of *Piper* or an extract obtained from at least two plants comprising *Piper*;

for use as a drug or nutritional product in the prevention and/or treatment of chronic inflammatory bowel disease in humans or animals.

In the present application, the singular or the plural will be used interchangeably to denote the useful compositions according to the invention.

The useful composition according to the invention thus comprises a single extract obtained from a mixture of several plants.

The composition, for use as a drug or nutritional product in the prevention and/or treatment of chronic inflammatory bowel diseases in humans or animals according to the invention, thus may be, for example, constituted of (comprise) at least:

a single extract obtained from at least *Chrysanthellum indicum, Cynara scolymus* and *Vaccinium myrtillus* and *Piper*; and/or a single extract obtained from at least *Chrysanthellum indicum, Cynara scolymus* and *Vaccinium myrtillus* and piperine; and/or a single extract obtained from at least *Chrysanthellum indicum, Cynara scolymus* and *Piper* and an extract obtained from *Vaccinium myrtillus*; and/or a single extract obtained from at least *Chrysanthellum indicum* and *Cynara scolymus* and an extract obtained from *Vaccinium myrtillus* and piperine; and/or a single extract obtained from at least *Chrysanthellum indicum* and *Cynara scolymus* and an extract obtained from *Vaccinium myrtillus* and *Piper*; and/or a single extract obtained from at least *Chrysanthellum indicum, Vaccinium myrtillus* and *Piper* and an extract obtained from *Cynara scolymus*; and/or a single extract obtained from at least *Chrysanthellum indicum* and *Vaccinium myrtillus* and an extract of *Cynara scolymus* and piperine; and/or a single extract obtained from at least *Chrysanthellum indicum* and *Vaccinium myrtillus* and an extract obtained from *Cynara scolymus* and *Piper*; and/or a single extract obtained from at least *Cynara scolymus, Vaccinium myrtillus* and *Piper* and an extract obtained from *Chrysanthellum indicum*; and/or a single extract obtained from at least *Cynara scolymus* and *Vaccinium myrtillus* and an extract of *Chrysanthellum indicum* and piperine; and/or a single extract obtained from at least *Cynara scolymus* and *Vaccinium myrtillus* and an extract obtained from *Chrysanthellum indicum* and *Piper*.

The whole plant or the aerial parts of *Chrysanthellum indicum* are preferably used as plant-derived raw material to obtain the extract(s) obtained from *Chrysanthellum indicum*. The single extract is preferably produced from at least 0.1% of the whole plant or the aerial parts of *Chrysanthellum indicum* by weight relative to the total weight of the mixture of plants used to make the single extract.

The leaves or roots of *Cynara scolymus* are preferably used as plant-derived raw material to obtain the extract(s) obtained from *Cynara scolymus*. The single extract is preferably produced from at least 0.1% of leaves or roots of *Cynara scolymus* by weight relative to the total weight of the mixture of plants used to make the single extract.

The fruits or leaves of *Vaccinium myrtillus* are preferably used as plant-derived raw material to obtain the extract(s) obtained from *Vaccinium myrtillus*. The single extract is preferably produced from at least 0.1% of fruits or leaves of *Vaccinium myrtillus* by weight relative to the total weight of the mixture of plants used to make the single extract.

The fruits or leaves of *Piper nigrum, Piper aduncum* and/or *Piper longum* are preferably used as plant-derived raw material to obtain the single extract or to obtain the extract(s) obtained from *Piper*. The single extract is preferably produced from at least 0.0001% of fruits or leaves of *Piper nigrum*, and/or of *Piper aduncum* and/or of *Piper longum* by weight relative to the total weight of the mixture of plants used to make the single extract.

Piperine, when it is not a *Piper* extract or when it does not come from *Piper*, is preferably a piperine obtained from *Peppery bolete* or *Chalciporus piperatus*. Optionally synthetic piperine may also be used.

Preferably, the composition according to the invention comprises at least the following molecules (these molecules being included in the extract(s) constituting the composition according to the invention):

at least one molecule chosen from apigenin-7-O-glucuronide, chrysanthellin A, chrysanthellin B, caffeic acid, luteolin, maritimetin, eryodictyol, isookanine, apigenin, luteolin-7-O-glucoside, maritimein, marein, eriodictyol-7-O-glucoside, flavomarein, apigenin-8-C-α-L-arabinoside-6-C-β-D-glucoside (shaftoside), apigenin-6,8-C-di-β-D-glucopyranoside (vicenin-2), or analogs thereof, preferably apigenin-7-O-glucuronide; and at least one molecule chosen from a dicaffeoylquinic acid, a sulfo-monocaffeoylquinic acid, luteolin, luteolin-7-O-glucoside, luteolin-7-O-glucuronide, apigenin-7-O-glucoside, cynaropicrin, or analogs thereof, preferably a dicaffeoylquinic acid; and at least one molecule chosen from a monocaffeoylquinic acid, delphinidin-3-galactoside, delphinidin-3-glucoside, cyanidin-3-galactoside, delphinidin-3-arabinoside, cyanidin-3-glucoside, petunidin-3-galactoside, cyanidin-3-arabinoside, petunidin-3-glucoside, peonidin-3-galactoside, petunidin-3-arabinoside, peonidin-3-glucoside, malvidin-3-galactoside, malvidin-3-glucoside, malvidin-3-arabinoside, or analogs thereof, preferably at least one monocaffeoylquinic acid; and piperine.

In addition to *Chrysanthellum indicum, Cynara scolymus, Vaccinium myrtillus* and/or *Piper*, the single extract of the composition according to the invention may also preferably be obtained from *Olea europaea* or, if the mixture of plants from which the single extract is obtained does not include *Olea europaea*, the composition may comprise an extract of *Olea europaea* or an extract obtained from at least two plants including *Olea europaea*.

The leaves or the fruits of *Olea europaea* are preferably used as plant-derived raw material to obtain the extract(s) obtained from *Olea europaea*. The single extract is preferably produced from at least 0.1% of leaves or fruits of *Olea europaea* by weight relative to the total weight of the mixture of plants used to make the single extract.

The single extract thus may also comprise, in addition to the other molecules, at least oleuropein and/or hydroxytyrosol.

The composition, for use as a drug or nutritional product in the prevention and/or treatment of chronic inflammatory bowel diseases in humans or animals according to the invention, thus may comprise, for example, at least one mixture of molecules consisting of at least:

- a single extract obtained from at least *Chrysanthellum indicum, Cynara scolymus* and *Vaccinium myrtillus, Olea europaea* and *Piper*; and/or
- a single extract obtained from at least *Chrysanthellum indicum, Cynara scolymus, Olea europaea* and *Vaccinium myrtillus* and piperine; and/or
- a single extract obtained from at least *Chrysanthellum indicum, Cynara scolymus, Olea europaea* and *Piper* and an extract obtained from *Vaccinium myrtillus*; and/or
- a single extract obtained from at least *Chrysanthellum indicum* and *Cynara scolymus, Olea europaea* and an extract of *Vaccinium myrtillus* and piperine; and/or
- a single extract obtained from at least *Chrysanthellum indicum* and *Cynara scolymus, Olea europaea* and an extract obtained from *Vaccinium myrtillus* and *Piper*; and/or
- a single extract obtained from at least *Chrysanthellum indicum, Vaccinium myrtillus, Olea europaea* and *Piper* and an extract obtained from *Cynara scolymus*; and/or
- a single extract obtained from at least *Chrysanthellum indicum, Olea europaea* and *Vaccinium myrtillus* and an extract of *Cynara scolymus* and piperine; and/or
- a single extract obtained from at least *Chrysanthellum indicum, Olea europaea* and *Vaccinium myrtillus* and an extract obtained from *Cynara scolymus* and *Piper*; and/or
- a single extract obtained from at least *Cynara scolymus, Olea europaea, Vaccinium myrtillus* and *Piper* and an extract obtained from *Chrysanthellum indicum*; and/or
- a single extract obtained from at least *Cynara scolymus, Olea europaea* and *Vaccinium myrtillus* and an extract of *Chrysanthellum indicum* and piperine; and/or
- a single extract obtained from at least *Cynara scolymus, Olea europaea* and *Vaccinium myrtillus* and an extract obtained from *Chrysanthellum indicum* and *Piper*; and/or
- a single extract obtained from at least *Chrysanthellum indicum, Cynara scolymus* and *Vaccinium myrtillus* and *Piper* and an extract obtained from *Olea europaea*; and/or
- a single extract obtained from at least *Chrysanthellum indicum, Cynara scolymus* and *Vaccinium myrtillus* and an extract obtained from *Olea europaea* and piperine; and/or
- a single extract obtained from at least *Chrysanthellum indicum, Cynara scolymus* and *Piper* and an extract obtained from *Vaccinium myrtillus* and *Olea europaea*; and/or
- a single extract obtained from at least *Chrysanthellum indicum, Cynara scolymus* and an extract obtained from *Vaccinium myrtillus* and *Olea europaea* and *Piper*; and/or
- a single extract obtained from at least *Chrysanthellum indicum, Cynara scolymus* and an extract obtained from *Vaccinium myrtillus* and *Olea europaea* and piperine; and/or
- a single extract obtained from at least *Chrysanthellum indicum, Cynara scolymus* and *Piper* and an extract obtained from *Vaccinium myrtillus* and an extract obtained from *Olea europaea*; and/or
- a single extract obtained from at least *Chrysanthellum indicum* and *Cynara scolymus* and an extract obtained from *Vaccinium myrtillus* and an extract obtained from *Olea europaea* and piperine; and/or
- a single extract obtained from at least *Chrysanthellum indicum* and *Cynara scolymus* and an extract obtained from *Vaccinium myrtillus* and an extract obtained from *Olea europaea* and *Piper*; and/or
- a single extract obtained from at least *Chrysanthellum indicum* and *Cynara scolymus* and an extract obtained from *Vaccinium myrtillus* and *Olea europaea* and an extract of *Piper*; and/or
- a single extract obtained from at least *Chrysanthellum indicum* and *Cynara scolymus* and an extract obtained from *Vaccinium myrtillus* and *Piper* and an extract obtained from *Olea europaea*; and/or
- a single extract obtained from at least *Vaccinium myrtillus, Cynara scolymus* and *Piper* and an extract obtained from *Chrysanthellum indicum* and *Olea europaea*; and/or
- a single extract obtained from at least *Vaccinium myrtillus, Cynara scolymus* and an extract obtained from *Chrysanthellum indicum* and *Olea europaea* and *Piper*; and/or
- a single extract obtained from at least *Vaccinium myrtillus, Cynara scolymus* and an extract obtained from *Chrysanthellum indicum* and *Olea europaea* and piperine; and/or
- a single extract obtained from at least *Vaccinium myrtillus, Cynara scolymus* and *Piper* and an extract obtained from *Chrysanthellum indicum* and an extract obtained from *Olea europaea*; and/or
- a single extract obtained from at least *Vaccinium myrtillus* and *Cynara scolymus* and an extract obtained from *Chrysanthellum indicum* and an extract obtained from *Olea europaea* and piperine; and/or
- a single extract obtained from at least *Vaccinium myrtillus* and *Cynara scolymus* and an extract obtained from *Chrysanthellum indicum* and an extract obtained from *Olea europaea* and *Piper*; and/or
- a single extract obtained from at least *Vaccinium myrtillus* and *Cynara scolymus* and an extract obtained from *Chrysanthellum indicum* and *Olea europaea* and an extract of *Piper*; and/or
- a single extract obtained from at least *Vaccinium myrtillus* and *Cynara scolymus* and an extract obtained from *Chrysanthellum indicum* and *Piper* and an extract obtained from *Olea europaea*; and/or
- a single extract obtained from at least *Vaccinium myrtillus, Chrysanthellum indicum* and *Piper* and an extract obtained from *Cynara scolymus* and *Olea europaea*; and/or
- a single extract obtained from at least *Vaccinium myrtillus, Chrysanthellum indicum* and an extract obtained from *Cynara scolymus* and *Olea europaea* and *Piper*; and/or
- a single extract obtained from at least *Vaccinium myrtillus, Chrysanthellum indicum* and an extract obtained from *Cynara scolymus* and *Olea europaea* and piperine; and/or
- a single extract obtained from at least *Vaccinium myrtillus, Chrysanthellum indicum* and *Piper* and an extract obtained from *Cynara scolymus* and an extract obtained from *Olea europaea*; and/or a single extract obtained from at least *Vaccinium myrtillus* and *Chrysanthellum indicum* and an extract obtained from *Cynara scolymus* and an extract obtained from *Olea europaea* and piperine; and/or a single extract obtained from at least *Vaccinium myrtillus* and *Chrysanthellum indicum* and an extract obtained from *Cynara scolymus* and an extract obtained from *Olea europaea* and *Piper*; and/or a single extract obtained from at least *Vaccinium myrtillus* and *Chrysanthellum indicum* and an extract obtained from *Cynara scolymus* and *Olea europaea* and an extract of *Piper*; and/or a single extract obtained from at least *Vaccinium myrtillus* and *Chrysanthellum indicum* and an extract obtained from *Cynara scolymus* and *Piper* and an extract obtained from *Olea europaea*.

Preferably, the composition according to the invention comprises:

a single extract obtained from *Chrysanthellum indicum*, *Olea europaea*, *Cynara scolymus*, *Vaccinum Myrtillus* and *Piper* (an extract obtained from five plants);

a single extract obtained from *Chrysanthellum indicum*, *Olea europaea* and *Cynara scolymus*, and an extract obtained from *Vaccinum myrtillus* and *Piper*, (an extract obtained from three plants and an extract obtained from two plants);

a single extract obtained from *Chrysanthellum indicum* and *Olea europaea*, and an extract obtained from *Cynara scolymus*, *Vaccinum myrtillus* and *Piper*, (an extract obtained from two plants and an extract obtained from three plants);

a single extract obtained from *Chrysanthellum indicum*, *Olea europaea*, an extract obtained from *Cynara scolymus*, and a single extract of *Vaccinum myrtillus* and *Piper* (an extract obtained from two plants, an extract obtained from one plant and an extract obtained from two plants);

a single extract obtained from *Chrysanthellum indicum* and *Cynara scolymus*, an extract of *Olea europea*, an extract of *Vaccinum myrtillus*, and an extract of *Piper* or piperine (an extract obtained from two plants and three extracts obtained from one plant);

a single extract obtained from *Chrysanthellum indicum*, *Olea europaea* and *Cynara scolymus*, an extract obtained from *Vaccinum myrtillus*, and an extract obtained from *Piper* or piperine (an extract obtained from three plants, and two extracts obtained from one plant).

A particularly suitable embodiment is one of these compositions that preferably comprises at least the following molecules (molecules contained in the extract(s) constituting the composition):

at least one molecule chosen from apigenin-7-O-glucuronide, chrysanthellin A, chrysanthellin B, caffeic acid, luteolin, maritimetin, eryodictyol, isookanine, apigenin, luteolin-7-O-glucoside, maritimein, marein, eriodictyol-7-O-glucoside, flavomarein, apigenin-8-C-α-L-arabinoside-6-C-β-D-glucoside (shaftoside), apigenin-6,8-C-di-β-D-glucopyranoside (vicenin-2), or analogs thereof, preferably apigenin-7-O-glucuronide; and at least one molecule chosen from a dicaffeoylquinic acid, a sulfo-monocaffeoylquinic acid, luteolin, luteolin-7-O-glucoside, luteolin-7-O-glucuronide, apigenin-7-O-glucoside, cynaropicrin, or analogs thereof, preferably a dicaffeoylquinic acid; and at least one molecule chosen from a monocaffeoylquinic acid, delphinidin-3-galactoside, delphinidin-3-glucoside, cyanidin-3-galactoside, delphinidin-3-arabinoside, cyanidin-3-glucoside, petunidin-3-galactoside, cyanidin-3-arabinoside, petunidin-3-glucoside, peonidin-3-galactoside, petunidin-3-arabinoside, peonidin-3-glucoside, malvidin-3-galactoside, malvidin-3-glucoside, malvidin-3-arabinoside, or analogs thereof, preferably at least one monocaffeoylquinic acid;

piperine; and oleuropein and/or hydroxytyrosol.

According to a particularly suitable variant, the mixture of molecules included in the useful composition according to the invention comprises at least a dicaffeoylquinic acid, apigenin-7-0-glucuronide, a monocaffeoylquinic acid, piperine and oleuropein. The mixture of molecules of the composition according to the invention may consist exclusively of a dicaffeoylquinic acid, apigenin-7-O-glucuronide, a monocaffeoylquinic acid, piperine and oleuropein.

The useful composition according to the invention, when it is intended for humans, preferably comprises an amount of single extract corresponding to a dose of at least 0.00001 g, in particular between 0.00001 g and 0.60 g of single extract per kg of body weight of the person to whom the composition is administered per day.

The single extract included in the useful composition according to the invention may be obtained by any suitable method, for example, by a method comprising the following steps:

solid/liquid extraction;
separation/pressing;
filtration;
evaporation;
drying;
optionally incorporation of additives;
homogenization;
packaging.

Alternatively and equivalently, one or more or all of the molecules of the single extract may be replaced by synthetic or natural molecules from other plants.

The compositions according to the invention in their different variants may consist exclusively of the elements described above or may also comprise at least one additional element (products, molecules, extracts, active ingredients, excipients, etc.) added to the plant extracts and/or the single extract(s) or of the mixture of at least four molecules; said additional element may be chosen from vitamin A, vitamin B1, vitamin B2, vitamin B3, vitamin B5, vitamin B6, vitamin B8, vitamin B9 (folic acid), vitamin B12, vitamin D, vitamin C, vitamin E, vitamin K, calcium, copper, magnesium, iron, zinc, selenium, manganese, phosphorus, polyunsaturated fatty acids of the omega 3 and/or omega 6 family, fructo-oligosaccharides, galacto-oligosaccharides, conjugated linolenic acid, lipoic acid, carotenoids, pectin, resveratrol, L-arginine, L-citrulline, curcumin, green tea, *Andrographis paniculata*, *Cannabis sativa*, psyllium, peppermint, probiotics, or excipients such as, for example, microcrystalline cellulose, magnesium stearate or dicalcium phosphate.

The useful compositions according to the invention may also comprise one or more extracts of at least one of the following plant-derived raw materials and/or one or more molecules contained in at least one of the following plant-derived materials and/or the single extract also may be obtained from at least one of the following plant-derived raw materials: *Abelmoschus esculentus, Abies Alba, Abies balsamea, Abies sibirica, Acacia nilotica, Acacia senegal,*

*Achillea millefollium, Achyranthes bidentata, Acmella oleracea, Actaea racemosa, Actinidia chinensis, Actinidia deliciosa, Adansonia digitata, Adiantum capillus-veneris, Aesculus hippocastanum, Afromomum melegueta, Agathosma betulina, Agathosma crenulata, Agathosma serratifolia, Agrimonia eupatoria, Ajuga reptans, Albizia julibrissin, Alchemilla vulgaris, Alliara petiolata, Allium ampeloprasum, Allium cepa, Allium sativum, Allium schoenoprasum, Allium ursinum, Anus glutinosa, Aloe ferox, Aloe vera, Aloysia citriodora, Alpinia galanga, Alpinia hainanensis, Alpinia officinarum, Alpinia oxyphylla, Althaea officinalis, Ammi visnaga, Amorphophallus konjac, Ananas comosus, Andographis paniculata, Anemarrhena asphodeloides, Anethum graveolens, Angelica archangelica, Angelica dahurica, Angelica pubescens, Angelica sinensis, Antennaria diocia, Anthriscus cerefolium, Anthyllis vulneraria, Aphanizomenon flos-aquae* Ralfs, *Apium graveolens, Arachis hypogaea, Aralia elata, Arctium lappa, Arctium minus, Argania spinosa, Armorica rustanica, Artemisia dracunculus, Artemesia vulgaris, Ascophyllum nodosum, Aspalathus linearis, Asparagus officinalis, Astragalus membranaceus, Atractylodeslancea, Atractylodes macrocephala, Auracaria columnaris, Avena staiva, Ayahuasca, Baccharis genistelloides, Bacopa monnierri, Ballota nigra, Bambusa bambos, Bellis perennis, Berberis vulgaris, Beta vulgaris, Betula alleghaniensis, Betula pendula, Betula pubescens, Bixa orellana, Borago officnalis, Boswellia serrata, Brassica napus, Brassica nigra, Brassica oleracea, Brassica rapa, Bupleurum chinense, Calendula officinalis, Calluna vulgaris, Camellia sinensis, Copsella bursa-pastoris, Capsicum annuum, Carex arenaria, Carica papaya, Carlina acaulis, Carphephorus odoratissmus, Carpinus betulus, Carthamus tinctorius, Carum carvi, Cassia fistula, Castanea sativa, Centaurea centaurium, Centaurea cyanus, Centaurium erythraea, Centella asiatica, Cerasus vulgaris, Ceratonia silliqua, Chaenomelum nobile, Chlorella vulgaris, Chondrus crispus, Chrysanthellum indicum, Cichorium intybus, Cinchona officinalis, cinchona pubescens, Cinnamomum camphora, Cinnamomum cassia, Cinnamomum verum, Cistanche salsa, Cistus incanus, Citrus aurantium, Citrus limon, Citrus maxima, Citrus medico, Citrus myrtifolia, Citrus reticulata blanco, Citrus sinsensis, Citrus paradisi, Clinopodium vulgare, Cnicus benedictus, Cochlearia officinalis, Cocos nucifera, Codonopsis pilosula, Coffea canephora, Coix lacryma-jobi* var. *mayyuen Stapf, Cola acuminata, Cola ballayi cornu, Cola nitida, Combretum micranthum, Commiphora mukul, Conyza canadensis, Coriandrum sativum, Cornus officinalis, Corylus avellana, Corymbia citriodora, Crataeguslaevigata, Craetegus monogyna, Crithmum maritimum, Crocus sativus, Cucumis melo, Cucurbita pepo, Cuminum cyminum, Cupressus sempervirens, Cuscuta chinensis, Cyamopsis tetragonoloba, Cyathula officinalis, Cyclanthera pedata, Cydonia oblonga, Cymbopogon martini, Cymbopogon nardus, Cymbopogon winterianus, Cynara cardunculus, Cyperus rotundus, Daucus carota, Dendranthema grandiflorum, Desmodium adscendens, Dimocarpuslongan, Dioscorea oppostifolia, Dioscorea villosa, Diospyros kaki* Thunb., *Dunaliella saliena, Echinacea augustifolia, Echinacea pallida, Echinacea purpurea, Elaegnus rhamnoides, Alettaria cardamomum, Eleutherococcus senticosus, Elymus repens, Epiobium augustifolium, Epilobium parviflorum, Equisetum arvense, Erica cinerea, Erica tetralix, Eriobotrya japonica, Eriodictyon californicum, Erodium cicutarium, Eryngium campestre, Eschscholzia californica, Eucalyptus dives* Schauer, *Eucalyptus globulus, Eucalyptus radiata, Eucalyptus smithii* F. Muell, *Eucommia ulmoides, Eugenia uniflora, Eugenia jambolana, Euphrasia stricta* D. Wolff, *Euterpe oleracea, Fagopyrum esculentum* Moench, *Follopia japonica, Ferula assa-foetida, Ficus carica, Filipendula ulmaria, Foeniculum vulgare* Mill., *Forsythia suspensa, Fragaria dodonei* Ard., *Frangula purshiana* Cooper, *Fraxinus excelsior, Fraxinus ortus, Fucus serratus, Fucus vesiculosus, Fumaria officinalis, Galeopsis segetum* Neck., *Galium odotarum, Galium verum, Gardenia jasminoides* J. Ellis, *Gastrodia elata* Blume, *Gelidium corneum* J. V. Lamouroux, *Gentiana lutea, Geranium robertianum, Geum urbanum, Ginkgo biloba, Glycine max, Glycyrrhiza glabra, Glycyrrhiza uralensis, Gracilaria gracilis, Grindelia camporum* Greene, *Grindelia robusta* Nutt., *Grindelia squarrosa* Dunal, *Gymnema sylvestris, Haematococcus pluvialis, Hamamemis virginiana, Harpagophytum procumbens, Harpagophytum zeyheri* Decne., *Hedeoma pluegioides* Pers., *Helianthus annuus, Helienthus tuberosus, Helichrysum arenarium, Helichrysum stoechas, Herniara glabra, Hibiscus sabdariffa, Hieracium pilosella, Himanthalia elongata, Hordeum vulgare, Houttuynia cordata* Thunb., *Huperzia serrata, Hyssopus officinalis, Ilex paraguariensis* A. St.-Hill, *Illicum verum, Impatients balsamina, Inula britannica, Inula helenium, Jasminum grandiflorum, Jasmium officinale, Juniperus communis, Justicia adhatoda, Kavalama urens, Krameria lappacea, Lagerstroemia speciosa, Laminaria digitata, Laminaria hyperborea, Lamium album, Larix dec Larix occidentalis, Laurus nobilis, Lavandula augustofolia, Lavandula latifolia, Ledum palustre, Leonurus cardiaca, Lepidium meyenii* Walp., *Lepidium sativum, Lespedeza capitata, Levisticum officinale, Lindera aggregata, Linus usitatissimum, Liquidambar styracifluac, Lotus bariculium Lycopersicon esculentum, Lycopodium clavatum, Lycopus europaeus, Lythrum salicaria, Macadamia ternifolia* F. muell, *Macrocystis pyrifera, Magnolia officinalis, Malpighia glabra, Malus pumila, Malus domestica, Malus sylvestris, Malva sylvestris, Mangvaera sylvestris, Mangifra, Marsdenia sylvestris, Mastocarpus stellatus, Matricaria chamomi* Ila, *Medicago sativa, Melaleuca alternifolia, Melaleuca cajuputi* Powell, *Melaleuca leucadendra, Melaleuca quinquenrvia, Melaleuca viridiflora, Melilotus altissimus* Thuill., *Melilotus officinalis, Mentha arvensis, Mentha x piperita, Menyanthes trifoliata, Menyanthes trifoliata, Morus alba, Morus nigra, Murraya koenigii, Musa x paradisiaca, Myrciaria dubia, Myristica flagrans* Houtt., *Myroxylon balsamum, Myrtus communis, Nardostachys jatamansi, Nasturtium officinale* R. Br., *Nelumbo nucifera* Gaertn., *Nepeta cataria, Nepeta tenuifolia* Benth., *Nigella sativa, Ocimum basilicum, Oenothera biennis, Ononis spinosa, ophiopogon japonicus, Opuntia ficus-indica, Origanum compactum* Benth., *Origanum majorana, Origanum vulgare, Orthosiphon aristatus, Oryza sativa, Paeonia lactiflora, Paeonia×suffruticosa* Andrews, *Palmaria palmata, Panax ginseng, Panax quinquefolius, Panicum miliacium, Papaver rhoeas, Parietaria officinalis, Passiflora edulis* Sims, *Pastinaca sativa, Paullinia cupana* Kunth, *Pelargonium graveolens, Perilla frutescens, Persea americana, Persicaria bistorta, Persicaria maculosa* Gray, *Petroselinum crispum, Peucadanum ostruthium, Peumus boldus* Molina, *Phaseolus vulgaris, Phellodendron amurense, Photinia melancarpa, Phyllanthus emblica, Physalis alkekengi, Phymatolithon calcareum, Picea abies, Pimenta dioca, Pimenta racemosa, Pimpinella anisum, Pimpinella major, Pimpinella saxfraga, Pinus mugo* Turra, *Pinus pinaster* Aiton, *Pinus sylvestris, Pistacia lentiscus, Plantago arenaria, Plantago lanceolata, Plantago major, Plantago ovata, Platycodon grandiflorus, Plectranthus barbatus* Andrews, *Pogostemom cablin, Polygola senega, Polygola* sibirica, Polygola tenuifolia Willd., Polygonum aviculare, Populus nigra, Populus tremula, Populus tremuloides, Porphyra umbilicalis, Portulaca oleracea, Potentilla erecta, Primula veris, Prunella vulgaris, Prunus africana, Prunus armeniaca, Ribes nigrum, Ribes uva-crispa, Rosa canina, Rosa gallica, Rosa moschata, Rosa rubiginosa, Rosmarinus officinalis, Rubus caesius, Rubus fruticosus, Rubus idaeus, Rumex actetosa, Rumex acetosella, Rumex crispus, Rumex patienta, Ruscus aculeatus, Sachharina japonica, Saccharina latissima, Salix alba, Salix fragilis, Salix pentandra, Salix purpurea, Salvia officinalis L., Salvia officinalis subsp. lavandulifolia Gams, Salvia sclarea, Sambucus nigra, Sanguisorba officinalis, Sanicula elata Buch.-Ham. Ex D. Don, Santalum album, Santolina chamaecyparissus, Saposhnikovia divaricata, Sargassum fusiforme, Satureja hortensis, Satureja montana, Saussurea costus, Scrophularia ningpoensis Helmsl., Scutellaria baicalensis Georgi, Secale cereale, Sedum acre, Sedum roseum, Senna alexandrina Mill., Senna obustifolia, Smilax cordifolia Humb. & Bonpl., Smilax glabra Roxb., Smilax officinalis Kunth, Smilax purhampuy Ruiz, Smilax purhampuy Ruiz, Smilax regelli Killip and C. V. Morton, Smilax vanillidora Apt, Solanum melongena, Solanum tuberosum, Solidago virgaurea, Sorbus aucuparia, Spatholobus suberctus Dunn., Spinacia oleracea, Spirulina major Kützing, Spirulina maxima Geitler, Spirulina platensis Geitler, Stavhys officinalis, Stemmacantha carthamoides Dittrich, Stypholobium japonicum, Syzgium aromaticum, Tagetes erecta, Tamarindus indica, Tanacetum parthemium, Terminalia chebula Retz., Theobroma cacao, Thymus saturejoides Coss., Thymus serpyllum, Thymus vulgaris, Thymus zygis, Tilia cordata Mill., Tilia platyphyllos Scop., Tilia tomentosa Moench, Tilia euopaea, Tribulus terrestris, Trichosanthes kirilowii Maxim., Trifolium arvense, Trifolium campestre Schreb., Trifolium pratense, Trifolium repens, Trigonella caerulea, Trigonella foenum-graecum, Tricitum aestivum, Tricitum durum Desf., Tricitum spelta L., Tricitum turgidum, Tropaeolum majus, Turnera diffusa Willd., Ulmus glabra Huds., Ulmus glabra Huds., Ulmus pumila, Ulmus rubra Muhl., Ulvalactuca, Uncaria gambir Roxb., Uncaria rhynchophylla Miq., Uncaria tomentosa DC., Undaria pinnatifida Suringar, Urtica dioca, Urtica urens, Vaccinium macrocarpon, Vaccinium oxycoccos, Vaccinium vitis-idae, Valeriana jatamansi Jones, Valeriana officinalis, Vanilla planifolia Jacks, Verbascum densiflorum Bertol., Verbascum thapsus, Verbena officinalis, Veronica officinalis, Viburnum opulus, Vigna angularis Ohwi & H. Ohashi, Vinca major, Vinca minor, Viola palustris, Viola tricolor, Vitex agnus-castus, Vitex trifolia, Vitis vinifera, Zea mays, Zingiber officinale Roscoe, Ziziphus jujuba Mill.

The compositions according to the invention are intended to be administered to humans or animals by any administration means, preferably orally. They may be in the form of powder, gel, emulsion, or in liquid form, and in particular in the form of tablets, capsules, gelcaps, sticks, sachets, ampoules, droppers or in injectable form.

When administered to a person or an animal, in particular a person or an animal affected by IBD, the compositions according to the invention are capable of modifying the profile of the intestinal microbiota of the host. This modification of the profile of the intestinal microbiota particularly involves:

a decrease in the imbalance of the Bacteroidetes/Firmicutes ratio, in particular an increase in Bacteroidetes and a decrease in Firmicutes; and/or an increase in the abundance of Akkermansia municiphila; and/or an increase in the abundance of Roseburia spp.

This effect thus allows the composition according to the invention to be used in the prevention and/or treatment of chronic inflammatory bowel diseases in humans or animals, in particular in the prevention and/or treatment of chronic abdominal pain and/or diarrhea and/or weight loss from chronic inflammatory bowel disease. The composition according to the invention particularly may be used in the prevention and/or treatment of Crohn's disease and/or ulcerative colitis.

The invention will now be illustrated with examples of compositions and test results demonstrating its effectiveness, with these examples and tests not being limiting.

EXAMPLES

Example 1

*Chrysanthellum* in powder form obtained from the aerial parts of *Chrysanthellum indicum*, artichoke in powder form obtained from the leaves of *Cynara scolymus*, blueberry in powder form obtained from the fruits of *Vaccinium myrtillus*, *Piper nigrum* fruit powder, and olive tree in powder form obtained from the leaves of *Olea europaea* are subjected to a maceration stage for 10 to 24 hours at room temperature in a 40/60 water/ethanol mixture, then the mixture obtained is subjected to continuous leaching at 50° C. in a percolator with a 40/60 water/ethanol mixture, the plant mixture/single extract ratio being 4 to 6/1. The extract obtained is then subjected to liquid/liquid washes using a non-polar organic solvent such as di- or tri-chloromethane. After concentration by low pressure evaporation at 35° C., a liquid is obtained that is lyophilized for 24 hours to give a violet-colored powder soluble in a water/alcohol mixture.

Example 2: Example of a Composition According to the Invention in the Form of Tablets, Comprising a Single Extract of Four Plants The composition of Example 2 is in the form of tablets that may be administered orally. It comprises a single hydro-alcoholic extract of a powder mixture obtained from the aerial parts of *Chrysanthellum indicum*, leaves of *Cynara scolymus*, fruits of *Vaccinium myrtillus*, and fruits of *Piper nigrum*. The ratio between the four plants is 1/1/0.1/0.0001. The composition also comprises, in addition to the mixture, zinc, selenium and folic acid. It also comprises excipients, in particular microcrystalline cellulose and magnesium stearate.

Example 3: Example of a Composition According to the Invention in the Form of Gelcaps Comprising a Single Extract The composition of Example 3 is in the form of gelcaps that may be administered orally. It comprises a single hydro-alcoholic extract of a powder mixture obtained from the aerial parts of *Chrysanthellum indicum*, leaves of *Cynara scolymus*, fruits of *Vaccinium myrtillus*, fruits of *Piper nigrum* and leaves of *Olea europaea*. The ratio between the five plants is 1/1/0.1/0.0001/0.6.

The single extract of the plant mixture is obtained through a method comprising the following steps:
solid/liquid extraction;
separation/pressing;

filtration;
evaporation;
drying;
optionally incorporation of additives;
homogenization;
packaging.

Example 4: Examples of a Composition According to the Invention in the Form of Tablets Comprising Synthetic Molecules or Obtained from Plant-Derived Raw Materials The composition of Example 4 is in the form of film-coated tablets that may be administered orally. It comprises the following as active substances for 1 tablet: 50 mg apigenin-7-O-glucuronide, 50 mg dicaffeoylquinic acid, 100 mg monocaffeoylquinic acid, 10 mg piperine and 250 mg oleuropein. The other components used as excipients are: pregelatinized starch, sodium carboxymethyl starch (type A), stearic acid, povidone K90, anhydrous colloidal silica. The active substances may be synthetic or be plant-derived raw materials or derived from plant extracts by purification by high-performance liquid chromatography.

Example 5: Example of a Composition According to the Invention in the Form of Gelcaps Comprising a Single Extract of Three Plants and Two Extracts of Plants The composition of Example 5 is in the form of gelcaps, with a plant-derived coating, that may be administered orally. It comprises a single hydro-alcoholic extract of a powder mixture obtained from the leaves of *Cynara scolymus*, the leaves of *Olea europaea* and the aerial parts of *Chrysanthellum indicum*. The ratio between the three plants is 1/1/1. The composition also comprises, in addition to the single extract, a dry hydro-alcoholic extract of *Vaccinium myrtillus* fruits and a dry hydro-alcoholic extract of *Piper nigrum* fruits. The ratio between the single extract and the two dry extracts is 1/0.1/0.0001. The composition does not include excipients.

Example 6: Example of a Composition According to the Invention in the Form of Tablets Comprising Two Extracts of Several Plants The composition of Example 6 is in the form of oblong tablets that may be administered orally. It comprises a single aqueous extract of a powder mixture obtained from the leaves of *Cynara scolymus*, the leaves of *Olea europaea* and whole plants of *Chrysanthellum indicum*. The ratio between the three plants is 1/0.6/1. The composition also comprises, in addition to the first single extract, a single hydro-alcoholic extract of a mixture of powder obtained from *Vaccinium myrtillus* marc and *Piper nigrum* fruits. The ratio between the two plants is 1/0.1. The ratio between the two single extracts is 1/1. The composition also comprises bulking agents, in particular microcrystalline cellulose and magnesium oxide, and anti-caking agents, in particular tricalcium phosphate and magnesium stearate.

Example 7: Example of a Composition According to the Invention in the Form of a Water-Soluble Powder Comprising a Single Extract from Two Plants and Three Plant Extracts The composition of Example 7, packaged in a stick, is in the form of a water-soluble powder that may be administered orally. It comprises a single hydro-alcoholic extract of a powder mixture obtained from *Cynara scolymus* leaves and *Chrysanthellum indicum* leaves. The ratio between the two plants is 1/1. The composition also comprises, in addition to the single extract, a hydro-alcoholic dry extract of *Olea europaea* leaves, a hydro-alcoholic dry extract of *Vaccinium myrtillus* fruits and a hydro-alcoholic dry extract of *Piper nigrum* fruits. The ratio between the single extract and the three dry extracts, in the aforementioned order, is 1/0.6/0.02/0.0001. The composition also comprises, as a support, wheat dextrin, natural flavors, colorings, including beet juice powder and sweeteners such as sucralose.

Evaluation of the Effect of the Composition According to the Invention on the Prevention and Treatment of IBD In vivo experiments in animals were carried out so as to evaluate the effectiveness of the composition according to the invention on the prevention and treatment of IBD. The model of mice fed a lipid-rich diet was chosen. This model is well known for inducing intestinal dysbiosis, systemic inflammation and greatly increasing the risk of developing IBD (Lee J, Lee H, Kim T, Kim M, Park Y, Kim J, Park K et al. *Plos One* 2017. 12 (11): e0187515. Doi: 10.1371/journal.pone.0187515. PMID: 29107964).

6 week old C57BL/6 male mice were fed a high-fat diet for 16 weeks. A group of mice was also supplemented with the incorporation into this lipid-rich diet of 2.7% of a composition x comprising a single hydro-alcoholic extract of a powder mixture obtained from the aerial parts of *Chrysanthemum indicum* (37% of the composition), *Cynara scolymus* leaves (37% of the composition), *Vaccinium myrtillus* fruits (3.7% of the composition), *Piper nigrum* fruits (0.04% of the composition), *Olea europaea* leaves (22.2% of the composition) and an excipient (silica). At the end of the treatment period, feces samples were taken. Bacterial DNA was extracted from biological samples according to a double lysis protocol (mechanical and chemical). The collected DNA solutions were then quantified by fluorimetry. Metagenomic analyses were then carried out on a fragment of a sequence amplified by PCR (fragment coding for 16S ribosomal RNA). Tables 1 and 2 show the relative abundance of the different phyla and genera of bacteria, respectively, between the groups of mice fed the high-fat diet (HFD) and the mice fed the high-fat diet and supplemented with the composition x (HFD+CX).

TABLE 1

Impact of supplementation with composition X on the relative abundance of the Bacteroidetes and Firmicutes phyla in mice fed a lipid-rich diet.

| Phylum | HFD | HFD + CX | Stats |
|---|---|---|---|
| Bacteroidetes | 14.19% (±2.45%) | 24.76% (±2.69%) | adj. p = 0.0272 |
| Firmicutes | 73.41% (±2.46%) | 57.22% (±2.70%) | adj. p = 0.0012 |

It can be seen that the composition according to the invention increased the proportion of Bacteroidetes (from 14.19% to 24.76%) and at the same time decreased the proportion of Firmicutes (from 73.41% to 57.22%)

TABLE 2

Impact of supplementation with composition X on the relative abundance of the *Akkermansia muciniphila* genus in mice fed a lipid-rich diet.

| Genus | HFD | HFD + CX | Stats |
|---|---|---|---|
| *Akkermansia* | 2.17% (±2.52%) | 14.81% (±2.52%) | adj. p = 0.0099 |

It can be seen that the composition according to the invention increased the relative proportion of *Akkermansia muciniphila* (from 2.17% to 14.81%).

Thus, the composition according to the invention, by acting on the microbiota in this way, may be used in the treatment of IBD.

The invention claimed is:

1. A method for treating a chronic inflammatory bowel disease in a human or an animal, the method comprising administering to the human or the animal one of the following compositions:
   a) a composition comprising:
      an extract obtained from co-extracting a mixture of at least *Chrysanthellum indicum, Cynara scolymus* and *Vaccinium myrtillus,*
      and *Piper;*
   b) a composition comprising an extract obtained from co-extracting a mixture of at least *Chrysanthellum indicum, Cynara scolymus* and *Vaccinium myrtillus* and piperine;
   c) a composition comprising:
      an extract obtained from co-extracting a mixture of at least *Chrysanthellum indicum, Cynara scolymus* and *Piper,*
      and an extract obtained from *Vaccinium myrtillus;*
   d) a composition comprising:
      an extract obtained from co-extracting a mixture of at least *Chrysanthellum indicum* and *Cynara scolymus,*
      and an extract obtained from *Vaccinium myrtillus* and piperine;
   e) a composition comprising:
      an extract obtained from co-extracting a mixture of at least *Chrysanthellum indicum* and *Cynara scolymus,*
      and an extract obtained from *Vaccinium myrtillus* and *Piper;*
   f) a composition comprising:
      an extract obtained from co-extracting a mixture of at least *Chrysanthellum indicum, Vaccinium myrtillus* and *Piper,*
      and an extract obtained from *Cynara scolymus;*
   g) a composition comprising:
      an extract obtained from co-extracting a mixture of at least *Chrysanthellum indicum* and *Vaccinium myrtillus,*
      and an extract of *Cynara scolymus* and piperine;
   h) a composition comprising:
      an extract obtained from co-extracting a mixture of *Chrysanthellum indicum* and *Vaccinium myrtillus,*
      and an extract obtained from *Cynara scolymus* and *Piper;*
   i) a composition comprising:
      an extract obtained from co-extracting a mixture of at least *Cynara scolymus, Vaccinium myrtillus* and *Piper,*
      and an extract obtained from *Chrysanthellum indicum;*
   j) a composition comprising:
      an extract obtained from co-extracting a mixture of at least *Cynara scolymus* and *Vaccinium myrtillus,*
      an extract of *Chrysanthellum indicum,*
      and piperine; or
   k) a composition comprising:
      an extract obtained from co-extracting a mixture of at least *Cynara scolymus* and *Vaccinium myrtillus,*
      And an extract obtained from co-extracting *Chrysanthellum indicum* and *Piper.*

2. The method of claim 1, wherein the human or the animal is in need of prevention and/or treatment of chronic abdominal pain and/or diarrhea and/or weight loss from chronic inflammatory bowel diseases.

3. The method of claim 1, wherein the chronic inflammatory bowel disease is Crohn's disease and/or ulcerative colitis.

4. The method of claim 1, wherein administering the composition increases *Akkermansia mucimphila* in the intestinal microbiota.

5. The method of claim 1, wherein administering the composition increases *Roseburia* spp in the intestinal microbiota.

6. The method of claim 1, wherein administering the composition rebalances the Bacteroidetes/Firmicutes ratio in the intestinal microbiota.

7. The method of claim 1, wherein the composition comprises the following molecules:
   at least one molecule selected from apigenin-7-O-glucuronide, chrysanthellin A, chrysanthellin B, caffeic acid, luteolin, maritimetin, eryodictyol, isookanine, apigenin, luteolin-7-O-glucoside, maritimein, marein, eriodictyol-7-O-glucoside, flavomarein, apigenin-8-C-α-L-arabinoside-6-C-β-D-glucoside (shaftoside), apigenin-6,8-C-di-β-D-glucopyranoside (vicenin-2); and
   at least one molecule selected from a dicaffeoylquinic acid, a sulfo-monocaffeoylquinic acid, luteolin, luteolin-7-O-glucoside, luteolin-7-O-glucuronide, apigenin-7-O-glucoside, cynaropicrin; and
   at least one molecule selected from a monocaffeoylquinic acid, delphinidin-3-galactoside, delphinidin-3-glucoside, cyanidin-3-galactoside, delphinidin-3-arabinoside, cyanidin-3-glucoside, petunidin-3-galactoside, cyanidin-3-arabinoside, petunidin-3-glucoside, peonidin-3-galactoside, petunidin-3-arabinoside, peonidin-3-glucoside, malvidin-3-galactoside, malvidin-3-glucoside, malvidin-3-arabinoside; and
   piperine.

8. The method of claim 1, wherein the composition further comprises an extract of *Olea europaea.*

9. The method of claim 1, wherein the composition is further defined by one or more of the following features:
   *Chrysanthellum indicum* corresponds to the whole plant and/or to the aerial parts of *Chrysanthellum indicum;* and/or
   *Cynara scolymus* corresponds to the roots and/or leaves of *Cynara scolymus;* and/or
   *Vaccinum myrtillus* corresponds to the leaves and/or fruit of *Vaccinum myrtillus.*

10. The method of claim 1, wherein the composition further comprises oleuropein and/or hydroxytyrosol.

11. The method of claim 1, wherein the the composition comprises dicaffeoylquinic acid, apigenin-7-O-glucuronide, monocaffeoylquinic acid, and/or piperine.

12. The method of claim 1, wherein the composition further comprises one or more of the following: vitamin A, vitamin B1, vitamin B2, vitamin B3, vitamin B5, vitamin B6, vitamin B8, vitamin B9 (folic acid), vitamin B12, vitamin D, vitamin C, vitamin E, vitamin K, calcium, copper, magnesium, iron, zinc, selenium, manganese, phosphorus, polyunsaturated fatty acids of the omega-3 and/or omega-6 family, fructo-oligosaccharides, galacto-oligosaccharides, conjugated linolenic acid, lipoic acid, carotenoids, pectin, resveratrol, L-arginine, L-citrulline, curcumin, tea green, *Andrographis paniculata, Cannabis sativa,* psyllium, peppermint, probiotics, an excipient, microcrystalline cellulose, magnesium stearate and/or dicalcium phosphate.

13. The method of claim 1, wherein the composition is in the form of powder, gel, emulsion, or in liquid form.

14. The method of claim 1, wherein the composition is in the form of tablets, capsules, gelcaps, sticks, sachets, ampoules, droppers or in injectable form.

15. The method of claim 1, wherein *Piper* is one or more of the following: *Piper nigrum, Piper aduncum* and/or *Piper longum*.

* * * * *